(12) United States Patent
Beamon et al.

(10) Patent No.: US 12,653,548 B2
(45) Date of Patent: Jun. 16, 2026

(54) COLLAR LOCK AND METHOD FOR LOCKING A SHAFT WITHIN A HOUSING

(71) Applicant: MEDTRONIC PS MEDICAL, INC.,
Fort Worth, TX (US)

(72) Inventors: Hubert B. Beamon, Haltom City, TX
(US); Michael Vu, Grand Prairie, TX
(US); Jennifer M. Cao, Mckinney, TX
(US); Aayush Malla, Fort Worth, TX
(US); Saideep Nakka, Northlake, TX
(US)

(73) Assignee: Medtronic PS Medical, Inc., Goleta,
CA (US)

( * ) Notice: Subject to any disclaimer, the term of this
patent is extended or adjusted under 35
U.S.C. 154(b) by 149 days.

(21) Appl. No.: 18/761,368

(22) Filed: Jul. 2, 2024

(65) Prior Publication Data

US 2025/0057542 A1      Feb. 20, 2025

Related U.S. Application Data

(60) Provisional application No. 63/533,186, filed on Aug.
17, 2023.

(51) Int. Cl.
*A61B 17/16* (2006.01)
*A61B 17/00* (2006.01)
(52) U.S. Cl.
CPC .................... *A61B 17/1613* (2013.01); *A61B
2017/00477* (2013.01)
(58) Field of Classification Search
CPC ... A61B 17/1613; A61B 17/16; A61B 17/162;
A61B 2017/0046
See application file for complete search history.

(56) References Cited

U.S. PATENT DOCUMENTS 233,709 A     10/1880   Starr
288,676 A     11/1883   Stearns
(Continued)

FOREIGN PATENT DOCUMENTS

CH           686113 A5     1/1996
CN          1150073 A     5/1997
(Continued)

OTHER PUBLICATIONS

International Search Report and Written Opinion for International
Application No. PCT/US2016/018686 dated Jul. 12, 2016 (4 pgs).
(Continued)

*Primary Examiner* — Zade Coley
(74) *Attorney, Agent, or Firm* — Carter, DeLuca & Farrell
LLP

(57) ABSTRACT

A surgical device includes a housing configured to receive a
tool having a cylinder configured to support a drive shaft. A
collar assembly is disposed atop the housing and is config-
ured to engage a cylinder head of the cylinder. The collar
assembly includes: a collar having a step ring separating an
inner peripheral surface and a spring assembly seat, the inner
peripheral surface dimensioned to engage the housing and
the spring assembly seat configured to receive a spring
assembly therein. One or more engagement spheres are
configured to seat within a ball pocket defined through the
housing. The sphere(s) is configured on one end to abut the
cylinder head upon introduction into the housing and on the
opposite end to seat within a groove defined within the
collar. The sphere(s) translates within the groove between
first and second pockets upon collar rotation to secure the
cylinder within the housing.

10 Claims, 9 Drawing Sheets

(56)                 References Cited

U.S. PATENT DOCUMENTS

| | | | |
|---|---|---|---|
| 1,043,098 A | 11/1912 | Gross | |
| 1,053,709 A | 2/1913 | Collins | |
| 1,112,349 A | 9/1914 | Barnes | |
| 1,209,362 A | 12/1916 | Turner | |
| 1,539,439 A | 5/1925 | Oscar | |
| 1,862,337 A | 6/1932 | Emrick | |
| 2,477,058 A | 7/1949 | Harborne et al. | |
| 2,512,033 A | 6/1950 | Metz | |
| 2,522,388 A | 9/1950 | Madsen | |
| 2,596,594 A | 5/1952 | Petre | |
| 2,682,184 A | 6/1954 | Szarkowski | |
| 2,726,872 A | 12/1955 | Onsrud | |
| 2,766,791 A | 10/1956 | Givens | |
| 2,773,693 A | 12/1956 | Chittenden | |
| 3,043,634 A | 7/1962 | Samuel | |
| 3,136,347 A | 6/1964 | Linquist | |
| 3,589,826 A | 6/1971 | Fenn | |
| 3,637,225 A | 1/1972 | Schmuck | |
| 3,835,858 A | 9/1974 | Hagen | |
| 3,943,986 A | 3/1976 | Lejdegard | |
| 4,035,100 A | 7/1977 | Kruger et al. | |
| 4,047,722 A | 9/1977 | Nielsen et al. | |
| 4,078,593 A | 3/1978 | Benitz | |
| 4,107,949 A | 8/1978 | Wanner et al. | |
| 4,123,074 A | 10/1978 | Wanner | |
| 4,146,240 A | 3/1979 | Nielsen | |
| 4,185,383 A | 1/1980 | Heimke et al. | |
| 4,378,053 A | 3/1983 | Simpson | |
| 4,431,062 A * | 2/1984 | Wanner | B25D 17/06 |
| | | | 173/104 |
| 4,502,734 A | 3/1985 | Allan | |
| 4,512,692 A | 4/1985 | Nielsen | |
| 4,565,472 A | 1/1986 | Brennsteiner et al. | |
| 4,594,036 A | 6/1986 | Hogenhout | |
| 4,655,651 A | 4/1987 | Hunger et al. | |
| 4,823,468 A | 4/1989 | Kollegger | |
| 4,830,000 A | 5/1989 | Shutt | |
| 4,917,274 A | 4/1990 | Asa et al. | |
| 5,009,440 A | 4/1991 | Manschitz | |
| 5,116,353 A | 5/1992 | Green | |
| 5,203,654 A | 4/1993 | Henderson | |
| 5,256,147 A | 10/1993 | Vidal et al. | |
| 5,263,786 A | 11/1993 | Kageyama | |
| 5,286,145 A | 2/1994 | Kleine | |
| 5,352,234 A | 10/1994 | Scott | |
| 5,382,249 A | 1/1995 | Fletcher | |
| 5,421,682 A | 6/1995 | Obermeier et al. | |
| 5,439,005 A | 8/1995 | Vaughn | |
| 5,466,101 A | 11/1995 | Meyen | |
| 5,487,626 A | 1/1996 | Von Holst et al. | |
| 5,499,985 A | 3/1996 | Hein et al. | |
| 5,505,737 A | 4/1996 | Gosselin et al. | |
| 5,549,634 A | 8/1996 | Scott et al. | |
| 5,569,256 A | 10/1996 | Vaughn et al. | |
| D377,982 S | 2/1997 | Walen | |
| 5,601,560 A | 2/1997 | Del Rio et al. | |
| 5,634,933 A | 6/1997 | McCombs et al. | |
| 5,697,158 A | 12/1997 | Klinzing et al. | |
| 5,720,749 A | 2/1998 | Rupp | |
| 5,735,535 A | 4/1998 | McCombs et al. | |
| 5,741,263 A | 4/1998 | Umber et al. | |
| 5,782,836 A | 7/1998 | Umber et al. | |
| 5,807,040 A | 9/1998 | Bongers-Ambrosius et al. | |
| 5,810,802 A | 9/1998 | Panescu et al. | |
| 5,833,704 A | 11/1998 | McCombs et al. | |
| 5,851,094 A | 12/1998 | Strand et al. | |
| 5,888,200 A * | 3/1999 | Walen | B25F 3/00 |
| | | | 606/167 |
| 5,893,851 A | 4/1999 | Umber et al. | |
| 5,928,241 A | 7/1999 | Menut et al. | |
| 5,941,891 A | 8/1999 | Walen | |
| 5,964,555 A | 10/1999 | Strand | |
| 5,989,257 A | 11/1999 | Tidwell et al. | |
| 6,000,940 A | 12/1999 | Buss et al. | |
| 6,007,541 A | 12/1999 | Scott | |
| 6,033,408 A | 3/2000 | Gage et al. | |
| 6,062,575 A | 5/2000 | Mickel et al. | |
| 6,209,886 B1 | 4/2001 | Estes et al. | |
| 6,261,035 B1 | 7/2001 | Moores, Jr. et al. | |
| 6,267,763 B1 | 7/2001 | Castro | |
| RE37,358 E | 9/2001 | Del Rio et al. | |
| 6,290,525 B1 | 9/2001 | Jacobi | |
| 6,409,221 B1 | 6/2002 | Robinson et al. | |
| 6,447,484 B1 | 9/2002 | Briscoe et al. | |
| 6,607,533 B2 | 8/2003 | Del Rio et al. | |
| 6,612,588 B2 | 9/2003 | Ostermeier et al. | |
| 6,688,610 B2 | 2/2004 | Huggins et al. | |
| 6,723,101 B2 | 4/2004 | Fletcher et al. | |
| 6,733,218 B2 | 5/2004 | Del Rio et al. | |
| D492,412 S | 6/2004 | Desoutter et al. | |
| 6,746,153 B2 | 6/2004 | Del Rio et al. | |
| 6,780,189 B2 | 8/2004 | Tidwell et al. | |
| 6,811,190 B1 | 11/2004 | Ray et al. | |
| 6,976,815 B2 | 12/2005 | Berglow et al. | |
| 7,001,391 B2 | 2/2006 | Estes et al. | |
| 7,011,661 B2 | 3/2006 | Riedel et al. | |
| 7,066,940 B2 | 6/2006 | Riedel et al. | |
| D536,791 S | 2/2007 | Eskridge et al. | |
| 7,261,169 B2 | 8/2007 | Kleine et al. | |
| 7,374,375 B2 | 5/2008 | Kleine et al. | |
| 7,429,154 B2 | 9/2008 | Kleine et al. | |
| 7,465,309 B2 | 12/2008 | Walen | |
| 7,488,327 B2 | 2/2009 | Rathbun et al. | |
| 7,497,860 B2 | 3/2009 | Carusillo et al. | |
| 7,549,992 B2 | 6/2009 | Shores et al. | |
| 7,559,927 B2 | 7/2009 | Shores et al. | |
| D609,810 S | 2/2010 | Cote et al. | |
| 7,669,308 B2 | 3/2010 | Oshnock et al. | |
| 7,691,106 B2 | 4/2010 | Schenberger et al. | |
| 7,722,054 B2 | 5/2010 | Young | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| 7,766,585 B2 | 8/2010 | Vasudeva et al. | |
| D631,962 S | 2/2011 | Dorman | |
| D636,082 S | 4/2011 | Cote et al. | |
| 7,922,720 B2 | 4/2011 | May et al. | |
| D641,468 S | 7/2011 | Ruiz, Sr. et al. | |
| 8,043,292 B2 | 10/2011 | Carusillo | |
| D648,021 S | 11/2011 | Dorman | |
| 8,100,912 B2 * | 1/2012 | Marietta | A61B 17/142 |
| | | | 606/176 |
| 8,137,370 B2 * | 3/2012 | Deng | A61B 17/162 |
| | | | 606/82 |
| D666,294 S | 8/2012 | Miles et al. | |
| 8,361,068 B2 | 1/2013 | McClurken | |
| 8,419,760 B2 | 4/2013 | Wiebe, III | |
| 8,518,065 B2 | 8/2013 | Shores | |
| D692,134 S | 10/2013 | Lee-Sepsick | |
| 8,597,316 B2 | 12/2013 | McCombs | |
| 8,702,710 B2 | 4/2014 | Carusillo | |
| 8,801,713 B2 | 8/2014 | del Rio et al. | |
| 8,893,820 B2 | 11/2014 | Barhitte et al. | |
| D728,098 S | 4/2015 | Schad et al. | |
| D728,099 S | 4/2015 | Schad et al. | |
| D744,650 S | 12/2015 | Catron et al. | |
| D746,457 S | 12/2015 | Swick et al. | |
| D747,477 S | 1/2016 | Freigang et al. | |
| D753,826 S | 4/2016 | Eggeling et al. | |
| 9,333,561 B2 | 5/2016 | Nakai et al. | |
| 9,597,737 B2 | 3/2017 | Hecht | |
| 10,080,579 B2 | 9/2018 | Cihak et al. | |
| 10,314,610 B2 | 6/2019 | Dexter et al. | |
| 10,588,640 B2 | 3/2020 | Steinhauser et al. | |
| 11,154,319 B2 | 10/2021 | Dexter et al. | |
| 11,925,362 B2 * | 3/2024 | Orphanos | A61B 17/1659 |
| 2002/0105149 A1 | 8/2002 | Karst | |
| 2002/0151902 A1 | 10/2002 | Riedel et al. | |
| 2002/0171208 A1 | 11/2002 | Lechot et al. | |
| 2003/0060841 A1 | 3/2003 | Del Rio et al. | |
| 2003/0097133 A1 | 5/2003 | Green et al. | |
| 2003/0130663 A1 | 7/2003 | Walen | |
| 2003/0140743 A1 | 7/2003 | Ofentavsek | |

(56) References Cited

U.S. PATENT DOCUMENTS

| | | | |
|---|---|---|---|
| 2003/0163134 A1 | 8/2003 | Riedel et al. | |
| 2003/0229351 A1 | 12/2003 | Tidwell et al. | |
| 2005/0027282 A1 | 2/2005 | Schweikert et al. | |
| 2005/0072007 A1 | 4/2005 | Proulx | |
| 2005/0232715 A1 | 10/2005 | Baumann et al. | |
| 2006/0053974 A1 | 3/2006 | Blust | |
| 2007/0021766 A1* | 1/2007 | Belagali | A61B 17/1624 |
| | | | 606/180 |
| 2007/0172321 A1 | 7/2007 | Nagai | |
| 2007/0282329 A1 | 12/2007 | Kawano | |
| 2008/0033280 A1 | 2/2008 | Lubock et al. | |
| 2009/0024129 A1 | 1/2009 | Gordon et al. | |
| 2009/0292304 A1* | 11/2009 | Malackowski | A61B 90/98 |
| | | | 606/170 |
| 2009/0312779 A1 | 12/2009 | Boykin et al. | |
| 2010/0063524 A1* | 3/2010 | McCombs | H02K 1/278 |
| | | | 606/167 |
| 2010/0076477 A1 | 3/2010 | Jezierski et al. | |
| 2011/0022069 A1 | 1/2011 | Mitusina | |
| 2011/0190803 A1 | 8/2011 | To et al. | |
| 2011/0218562 A1 | 9/2011 | Viola et al. | |
| 2011/0238070 A1 | 9/2011 | Santangelo et al. | |
| 2011/0270293 A1 | 11/2011 | Malla et al. | |
| 2011/0270294 A1 | 11/2011 | Rubin | |
| 2012/0070220 A1 | 3/2012 | Ruiz, Sr. et al. | |
| 2012/0259336 A1 | 10/2012 | del Rio et al. | |
| 2012/0259337 A1 | 10/2012 | del Rio | |
| 2013/0110147 A1 | 5/2013 | Dame | |
| 2013/0116659 A1 | 5/2013 | Porter | |
| 2013/0138096 A1 | 5/2013 | Benn | |
| 2013/0144267 A1 | 6/2013 | Chan et al. | |
| 2013/0245704 A1 | 9/2013 | Koltz et al. | |
| 2013/0296848 A1 | 11/2013 | Allen, IV et al. | |
| 2013/0304069 A1 | 11/2013 | Bono et al. | |
| 2014/0056656 A1 | 2/2014 | Bae et al. | |
| 2014/0124231 A1 | 5/2014 | Hessenberger et al. | |
| 2014/0163558 A1 | 6/2014 | Cosgrove et al. | |
| 2014/0262408 A1 | 9/2014 | Woodard | |
| 2014/0303624 A1 | 10/2014 | del Rio et al. | |
| 2014/0336654 A1 | 11/2014 | Pilgeram | |
| 2014/0343454 A1 | 11/2014 | Miller et al. | |
| 2014/0350561 A1 | 11/2014 | Dacosta et al. | |
| 2014/0371752 A1 | 12/2014 | Anderson | |
| 2016/0278802 A1 | 9/2016 | Cihak et al. | |
| 2017/0071608 A1* | 3/2017 | Edwards | B23B 31/1071 |
| 2017/0143350 A1* | 5/2017 | Burke | A61B 17/1631 |
| 2018/0140308 A1 | 5/2018 | Anderson | |
| 2018/0185052 A1 | 7/2018 | Zhou et al. | |
| 2019/0388115 A1 | 12/2019 | Nguyen | |
| 2021/0236144 A1* | 8/2021 | Bürk | A61B 17/1633 |
| 2022/0338895 A1 | 10/2022 | Bono et al. | |

FOREIGN PATENT DOCUMENTS

| | | |
|---|---|---|
| CN | 103447599 A | 12/2013 |
| CN | 103458805 A | 12/2013 |
| DE | 88152618 | 3/1989 |
| DE | 102012101259 A1 | 8/2013 |
| EP | 0293327 A2 | 11/1988 |
| EP | 0216354 B1 | 7/1991 |
| EP | 1101459 B1 | 2/2006 |
| EP | 1289714 B1 | 8/2008 |
| EP | 1514034 B1 | 10/2011 |
| FR | 1330849 A | 6/1963 |
| GB | 2129730 A | 5/1984 |
| JP | 2014516611 A | 7/2014 |
| RU | 2077275 C1 | 4/1997 |
| WO | 9608343 A1 | 3/1996 |
| WO | 0166024 A1 | 9/2001 |
| WO | 0189769 A1 | 11/2001 |
| WO | 2012138337 A1 | 10/2012 |
| WO | 2014037134 A1 | 3/2014 |
| WO | 2014176060 A1 | 10/2014 |

OTHER PUBLICATIONS

International Search Report PCT/US2023/080169, dated Mar. 4, 2024, 12pp.

International Search Report PCT/US2023/080139 dated Apr. 23, 2024, 19pp.

European Search Report 24194741.5, dated Nov. 27, 2024, 9pp.

* cited by examiner

COLLAR LOCK AND METHOD FOR LOCKING A SHAFT WITHIN A HOUSING

CROSS-REFERENCE TO RELATED APPLICATION

This application claims the benefit of and priority to U.S. Provisional Patent Application No. 63/533,186 filed Aug. 17, 2023, the entire disclosure of which is incorporated by reference herein.

FIELD

The present disclosure is generally directed to devices and systems for cutting and treating bone and hard tissue and biomaterials. More particularly, the devices and systems of the present disclosure may be particularly suitable for orthopedical applications and other surgical procedures requiring the attachment and locking of shaft-driven surgical tools onto motor driving hand-held housings for enabling bone removal.

BACKGROUND

Devices and systems in accordance with the present disclosure may be suitable for a variety of procedures including orthopedical surgical procedures, spinal procedures, cranial procedures, and other procedures requiring bone or hard tissue removal. During a given procedure, a motor is used to power a drill disposed at a distal end of the surgical tool. Typically, the tool is rotated at a very high RPM which allows the drill dissecting tip of the tool to plunge into the bone or, in some instances, cut or shave the bone using one or more flutes on the drill dissecting tip. In many instances it is important to align and lock the shaft of the rotating tool within a housing or bore during assembly to mechanically engage one or more internal components disposed within the housing, e.g., a drive shaft. It is important that that the user be able to quickly and confidently engage and lock the tool as needed and, equally important that the user be able to quickly uncouple the tool as needed.

SUMMARY

Provided in accordance with the present disclosure is a surgical device which includes an outer housing configured to receive a surgical tool within a cavity defined within the outer housing, the surgical tool including a cylinder configured to support a drive shaft for rotation therein. The surgical device also includes a collar assembly disposed atop the outer housing and configured to engage a cylinder head of the cylinder. The collar assembly includes: a collar having a step ring separating an inner peripheral surface and a spring assembly seat, the inner peripheral surface dimensioned to engage a first stepped surface atop the outer housing and the spring assembly seat configured to receive a spring assembly therein; and one or more engagement spheres configured to operably seat within a corresponding ball pocket defined through the outer housing into the cavity, the engagement sphere(s) configured on one end to abut the cylinder head of the cylinder upon introduction of the cylinder head into the housing and on the opposite end to seat within a complementary one or more grooves defined within the inner peripheral surface of the collar, the engagement sphere(s) configured to guide the collar along the groove such that the engagement sphere transitions between a first groove pocket and a second groove pocket upon rotation of the collar to secure the cylinder within the housing.

In aspects according to the present disclosure, the one or more grooves vary in depth between the first groove pocket and the second groove pocket such that more force is imparted by the engagement sphere(s) on the cylinder upon rotation of the collar.

In aspects according to the present disclosure, the first groove pocket and the second groove pocket vary in depth. In other aspects according to the present disclosure, an angle of depth between the first groove pocket and the second groove pocket ranges from about 30 degrees to about 100 degrees.

In aspects according to the present disclosure, the spring assembly includes a spring disposed configured to provide a bias between the cylinder and the housing.

In aspects according to the present disclosure, the spring assembly includes a locking ring configured to retain the collar assembly atop the outer housing.

In aspects according to the present disclosure, the cylinder head includes one or more recesses defined in the outer surface thereof, the one or more recesses configured to complement the first groove pocket on the opposite end the engagement sphere(s) to at least partially retain the engagement sphere(s) between the recess and first groove pocket when the cylinder head fully engages within the outer housing.

In aspects according to the present disclosure, the surgical tool includes an alignment tab extending therefrom, the alignment tab configured to operably engage a notch defined in the outer housing when the cylinder head fully engages within the outer housing, the alignment tab and notch configured to prevent rotation of the surgical tool during rotation of the collar.

In aspects according to the present disclosure, a center axis of each groove is offset relative to an axis of rotation of the collar.

In aspects according to the present disclosure, an angle of rotation of the collar within each one or more grooves to transition the corresponding one or more engagement spheres between the first groove pocket and the second grove pocket ranges from about 15 degrees to about 300 degrees.

BRIEF DESCRIPTION OF THE DRAWINGS

In the drawings, where like numerals refer to like components throughout several views.

DETAILED DESCRIPTION

Figure 1:
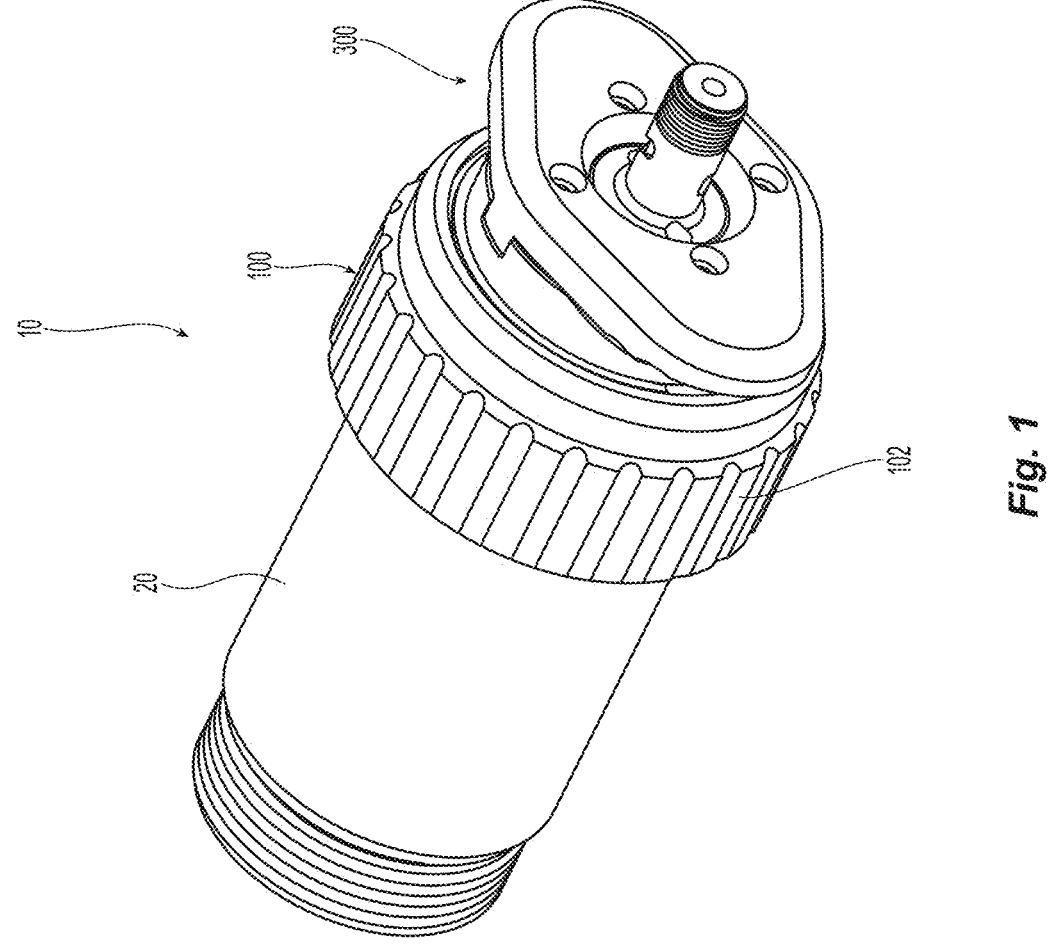
FIG. 1 is a perspective view of a collar locking assembly shown in a fully rotated locked position with a shaft cylinder of a surgical tool engaged and locked within an outer tool housing.
Figure 2:
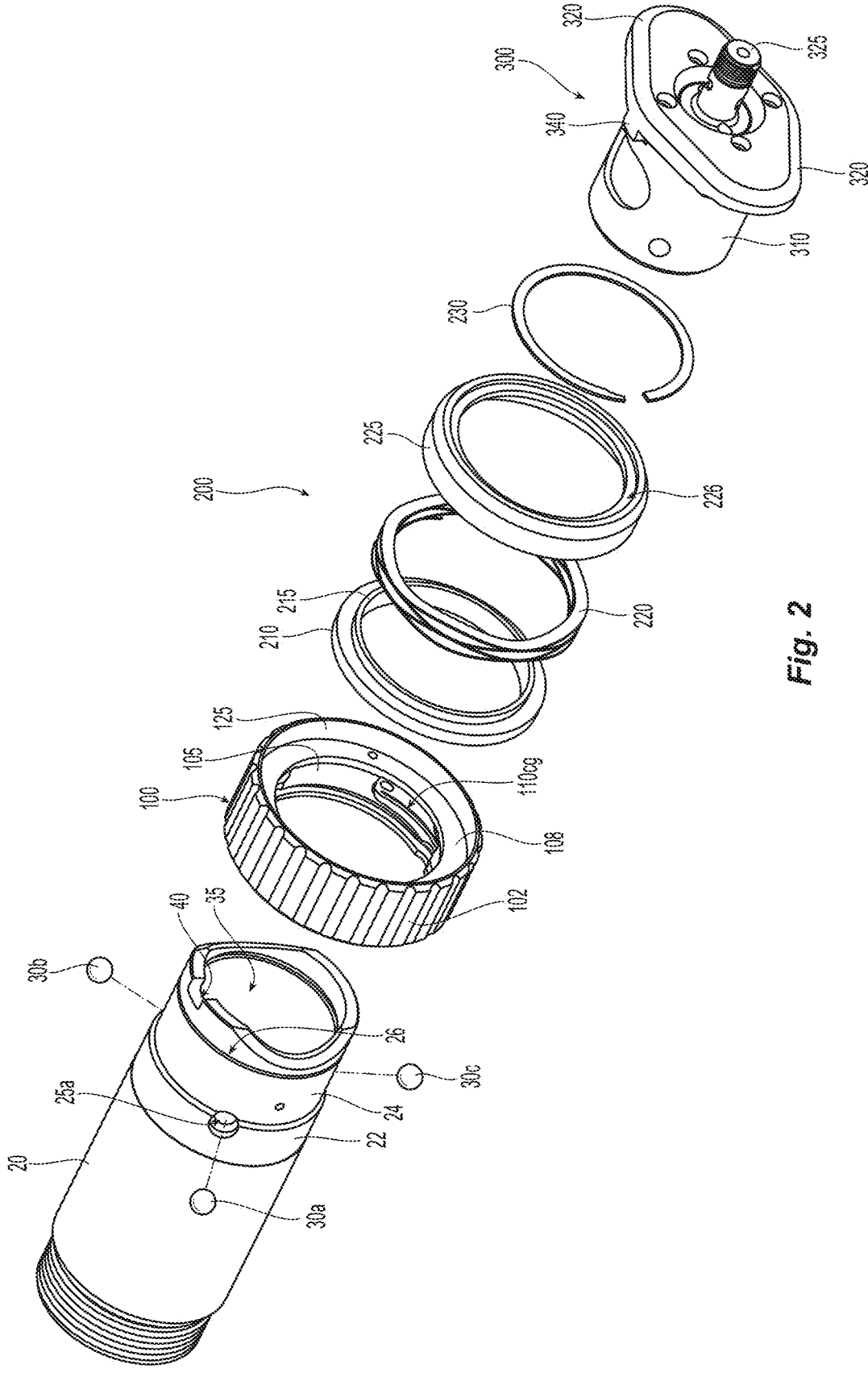
FIG. 2 is an exploded view of the collar locking assembly of FIG. 1.

FIGS. 1-2 illustrate one embodiment of an assembled surgical device 10 configured for use in orthopedic and cranial surgical procedures for dissecting, cutting, shaving, and otherwise removing bone and hard tissue. Device 10 includes an outer housing 20, a collar assembly 100, and a surgical tool 300. Outer housing 20 is configured to be handled by a surgeon (or robot-assisted) and typically includes a motor (not shown) operably associated therewith. The surgical tool 300 aligns and operably engages the outer housing 20 and includes, inter alia, a drive shaft 325, cylinder head 310, and an outer flange 320. The collar assembly 100 locks the surgical tool 300 atop the outer housing 20.

Drive shaft 325 is configured to align and operably engage a corresponding drive shaft (not shown) or other drive mechanism disposed within the outer housing 20. Cylinder head 310 is configured to be operably received within an internal bore 35 defined within the outer housing 20 and an alignment tab 340 disposed on the flange 320 is configured to mechanically engage a corresponding notch 40 defined within the outer housing 20 when the cylinder 310 is fully engaged therein as explained in more detail below with respect to FIG. 6.

Outer housing 20 is substantially cylindrical and includes first and second stepped surfaces 22 and 24 disposed thereabout configured to support a collar 102 of the collar assembly 100 and a spring assembly 200 disposed within the collar assembly 100. The first stepped surface 22 includes a series of openings defined therein (only opening 25a is shown in FIG. 2) configured to house an engagement sphere, e.g., sphere 30a, therein, the purposes of which is explained in detail below. The second stepped surface 24 is configured to abut a stop disposed along the inner peripheral surface of collar 102 on a proximal side thereof and abut a spring post 210 of the spring assembly 200 on the other side thereof (which also corresponds with the engagements spheres 30a-30c engaging respective grooves 110ag-110cg as detailed below).

Spring assembly 200 includes the spring post 210 which has an inner mounting flange 215 that is configured to support a compression spring 220 thereabout. A spring housing 225 snaps (or otherwise mechanically engages) spring post 210 encompassing the spring 220 therein. The spring housing 225 is configured to seat within an inner peripheral cavity 125 defined within the collar 102. Upon assembly, the spheres 30a-30c are seated within the corresponding openings, e.g., opening 25a shown, and the collar 102 with spring assembly 200 are slid atop outer housing 20 until stop 108 abuts the proximal end of step 24. Alternatively as mentioned above, engagements spheres 30a-30c may engage respective grooves 110ag-110cg to seat the collar 125. A locking ring 230 engages a distal step 26 of the outer housing 20 to lock the collar assembly 100 and spring assembly 200 atop the outer housing 20. The locking ring 230 is configured to seat within a ring cavity 226 defined about the distal end of the spring housing 225.

Collar assembly 100 includes the collar 102 and defines an inner peripheral surface 105 on the proximal side of the stop 108 that includes a series of grooves 110ag, 110bg and 110cg defined therein each including first and second respective groove pockets defined at the terminal ends thereof, e.g., groove 110ag including first groove pocket 110a1 and second groove pocket 110a2, groove 110bg including first groove pocket 110b1 and second groove pocket 110b2, and groove 110cg including first groove pocket 110c1 and second groove pocket 110c2. The first groove pocket, e.g., first pocket 110c1, associated with each groove, e.g., groove 110cg, is generally deeper than the second groove pocket, e.g., pocket 110c2, and is configured for a so-called "soft locked" position of the collar assembly 100 as explained in more detail below. Hereinafter groove pockets are simply referred to as "pockets".

Figures 3A, 3B:
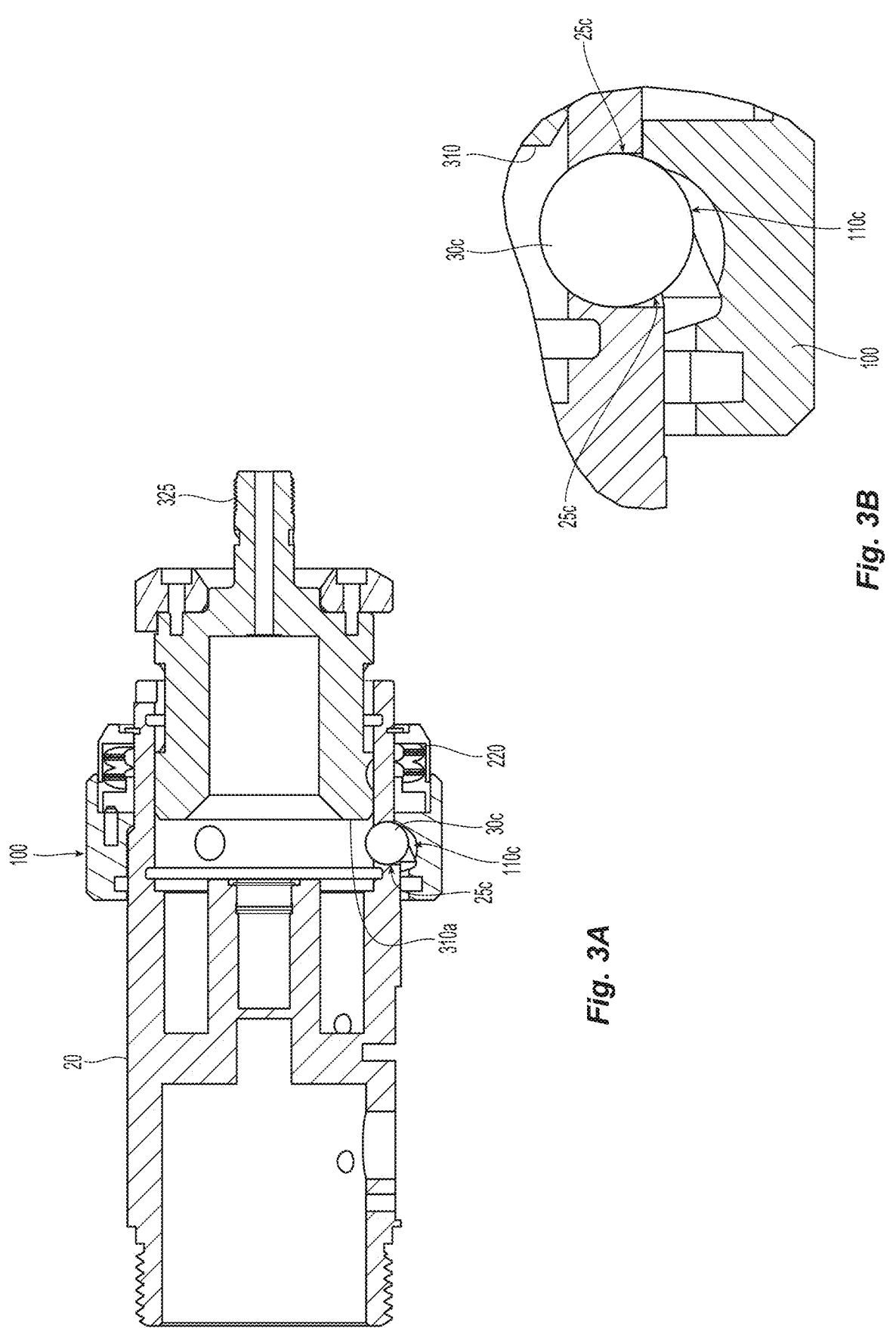
FIG. 3A is a side, cross-sectional view of the collar locking assembly, outer housing and surgical tool of FIG. 1 shown during initial engagement of the shaft cylinder within the outer housing.
FIG. 3B is an enlarged view of the area of detail of FIG. 3A showing one of a series of engagement spheres disposed within an outer pocket defined within the outer housing.

Turning now to FIGS. 3A and 3B which show the cylinder head 310 upon initial engagement within the outer housing 20 (prior to engagement with the engagement spheres 30a-30c (hereinafter "spheres 30a-30c")), the spheres 30a-30c remain lodged within their individual openings, e.g., openings 25a and 25c shown, in the outer housing 20 with minimal contact with the collar 102 in this position. Moreover, very little force "F" is exerted on the spring 220 (if any). As shown in FIG. 3B, a distal face 310a of the cylinder head 310 remains spaced from the spheres, e.g., sphere 30c.

Figures 4A, 4B:
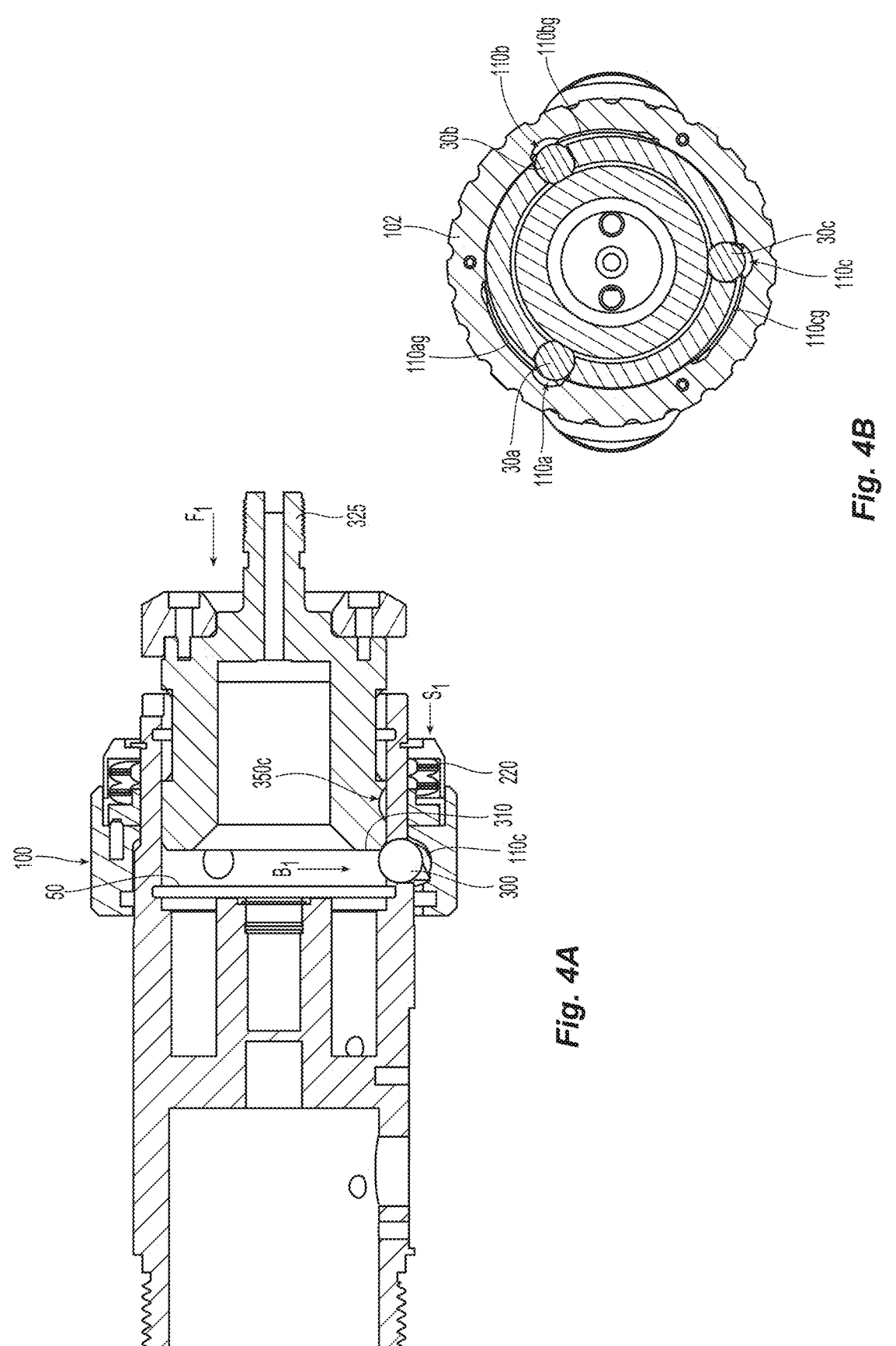
FIG. 4A is a side, cross-sectional view of the shaft cylinder during initial movement F1 into the outer housing against the bias of a spring of the collar locking assembly forcing the engagement spheres into first pockets defined within grooves of the collar locking assembly.
FIG. 4B is front, cross-sectional view of a collar of the collar locking assembly showing the engagement spheres being forced into the first pockets defined within the groove of the collar locking assembly shown in FIG. 4A.
Figure 6:
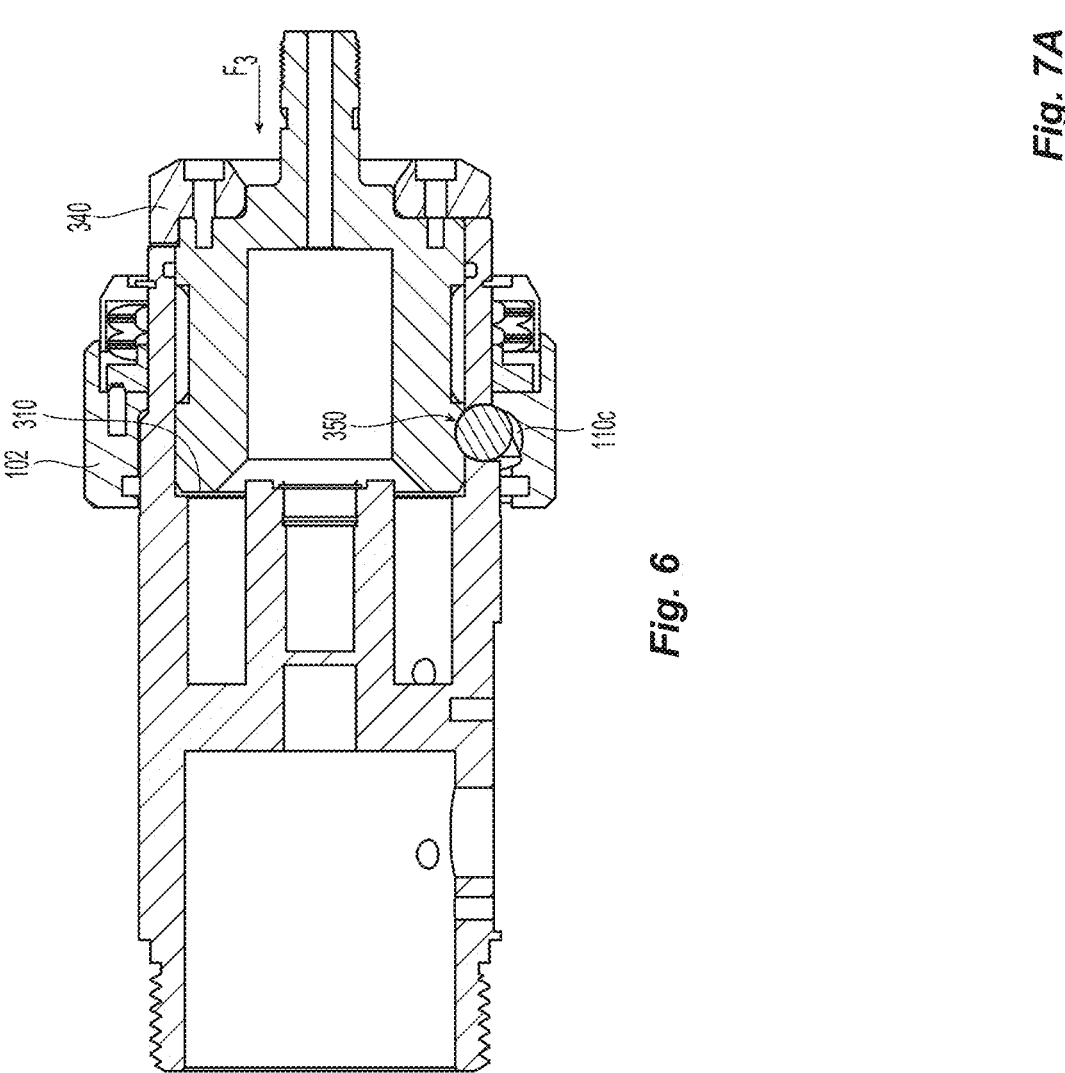
FIG. 6 is a side, cross-sectional view of the shaft cylinder during continued movement F3 into the outer housing against the bias of the spring of the collar locking assembly forcing the engagement spheres into the first pockets defined within grooves of the collar locking assembly to a soft locking position and where the shaft cylinder bottoms out against the internal face of the outer housing and a locking tab in the shaft cylinder mechanically seats within a notch defined within the outer housing.
Figure 8B:
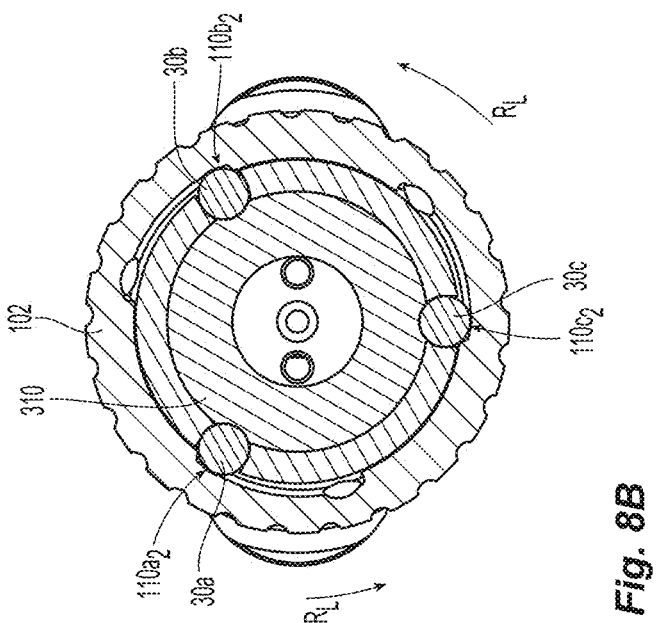
FIGS. 8A-8B are various views of the collar of the collar locking assembly in a fully rotated and locked position RI, with the engagement spheres seated within the second pockets.
Figure 8A:
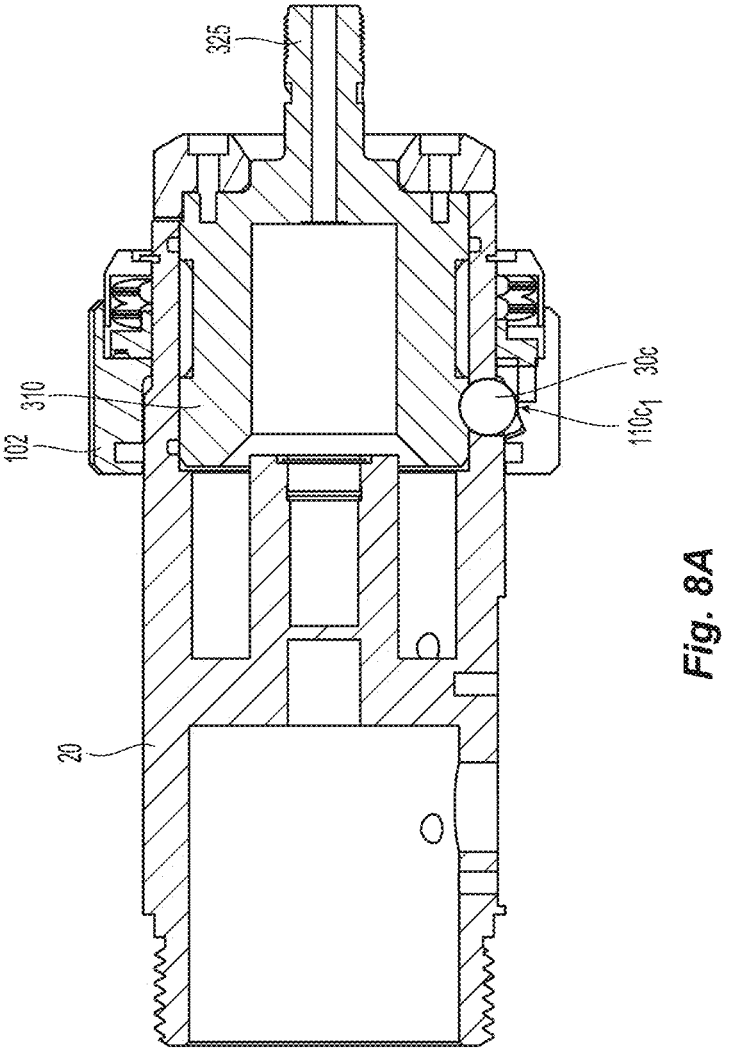

The tool 300 is engaged and locked within the outer housing 20 in two separate stages or in two locking positions, namely, a so-called "soft locked" position which is, ultimately, shown in FIG. 6 and so-called "fully locked" position as shown in FIGS. 8A and 8B. The locking positions are sequential. To initially engage the tool 300 within the outer housing 20 in soft locked engagement, the user exerts a force $F_1$ on the tool 300 against spring 220 in the direction $S_1$ forcing the cylinder head 310 into the internal bore 35 within the outer housing 20. The distal end 310a of the cylinder head 310 contacts the spheres 30a-30c forcing the spheres 30a-30c into respective first pockets 110a1-110c1 defined within respective grooves 110ag-110cg of collar 102 in the direction $B_1$ (FIGS. 4A and 4B). The cylinder head 310 also defines a series of soft lock recesses 350a-350c which are configured to align and seat each sphere 30a-30c when each sphere 30a-30c reaches the soft locked position as shown in FIG. 6.

Figures 5A, 5B:
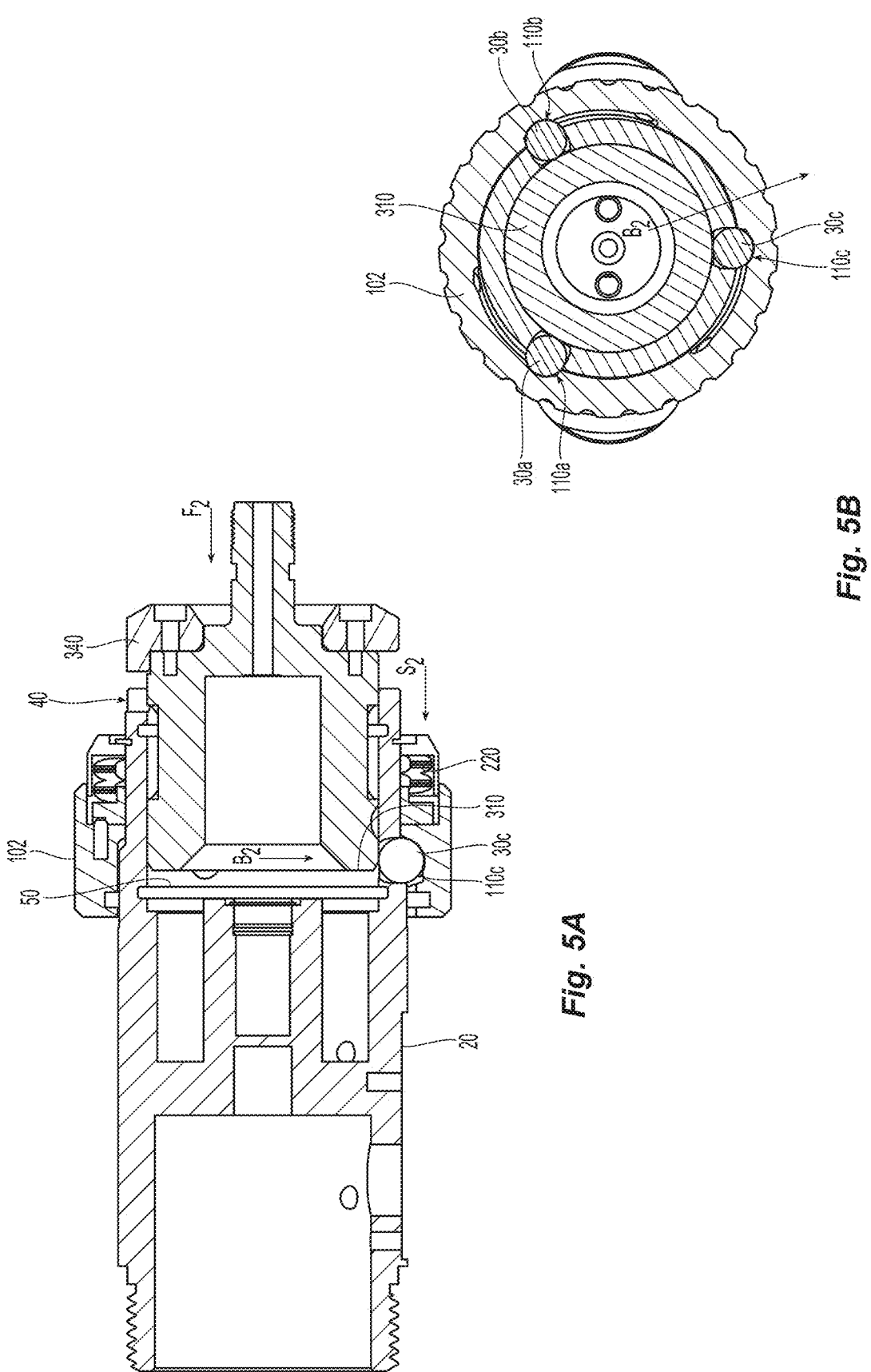
FIG. 5A is a side, cross-sectional view of the shaft cylinder during continued movement F2 into the outer housing against the bias of the spring of the collar locking assembly forcing the engagement spheres into the first pockets defined within grooves of the collar locking assembly.
FIG. 5B is front, cross-sectional view of the collar of the collar locking assembly showing the engagement spheres being forced into first pockets defined within the grooves of the collar locking assembly shown in FIG. 5A.

Continued movement of the tool 300 towards the soft locked position is shown in FIGS. 5A-5B wherein the tool 300 is forced further into bore 35 as the user exerts additional force $F_2$ (or continues to exert force $F_1$) on tool 300 against spring 220 in the direction $S_2$ forcing the cylinder head 310 further into the internal bore 35 within the housing 20. The cylinder 310 further forces the spheres 30a-30c into respective first pockets 110a1-110c1 defined within respective grooves 110ag-110cg of collar 102 in the direction $B_2$ (FIGS. 5A and 5B). Alignment tab 340 of cylinder head 310 also moves closer to engagement with notch 40 of outer housing 20.

As mentioned above, FIG. 6 shows the soft locked position of the tool 300 within the outer housing 20 wherein the cylinder head 310 is fully inserted within the internal bore 35 so that the distal end 310a abuts against faceplate 50 (FIGS. 4A and 5A) of internal bore 35. Other designs are contemplated including one or more flanges 320 on the cylinder. More particularly, the user exerts a force $F_3$ on the tool 300 against spring 220 in the direction $S_3$ (or continues to exert forces $F_1$ or F2) forcing the cylinder head 310 into the internal bore 35 against the spring 220 within the outer housing 20. The cylinder head 310 forces the spheres 30a-30c into respective first pockets 110a1-110c1 and grooves 110ag-110cg until the point that recesses 350a-350c seat the spheres 30a-30c therein when in the soft locked position. The notch 40 in the outer housing 20 receives the alignment member 340 of the cylinder head 310 which is designed to restrict the movement during rotation of the collar 102 as explained in more detail below. When disposed in the soft locked position, the spheres 30a-30c retain the tool 300 within the outer housing 20 with enough force to allow manipulation and handling thereof.

Figure 7A:
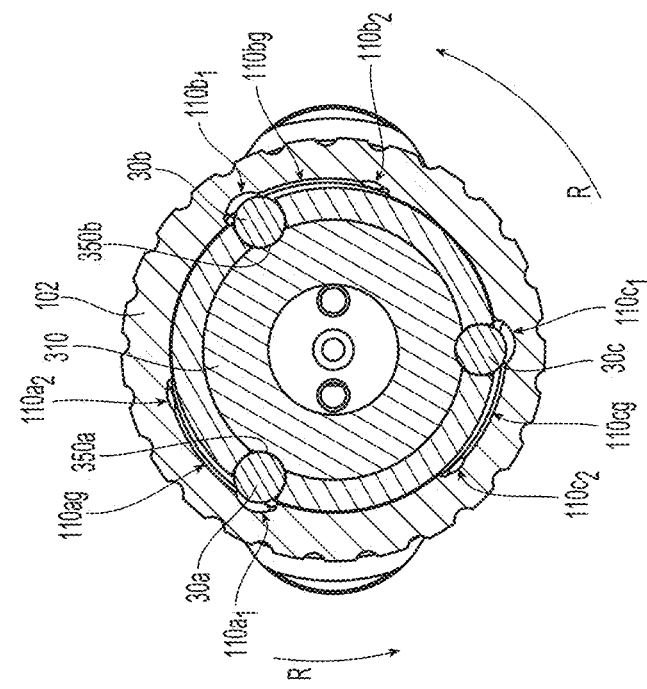
FIGS. 7A-7C are various views of the collar of the collar locking assembly upon initial rotation from the soft locking position to the fully locked position.
Figure 7C:
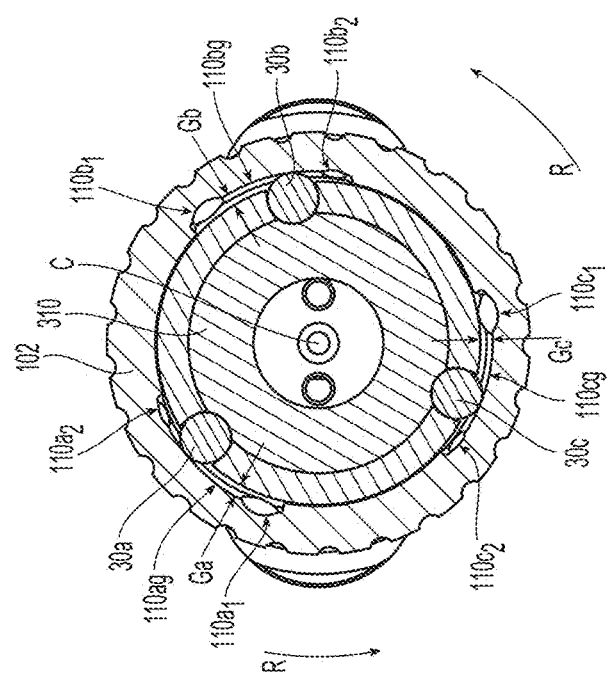
Figure 7B:
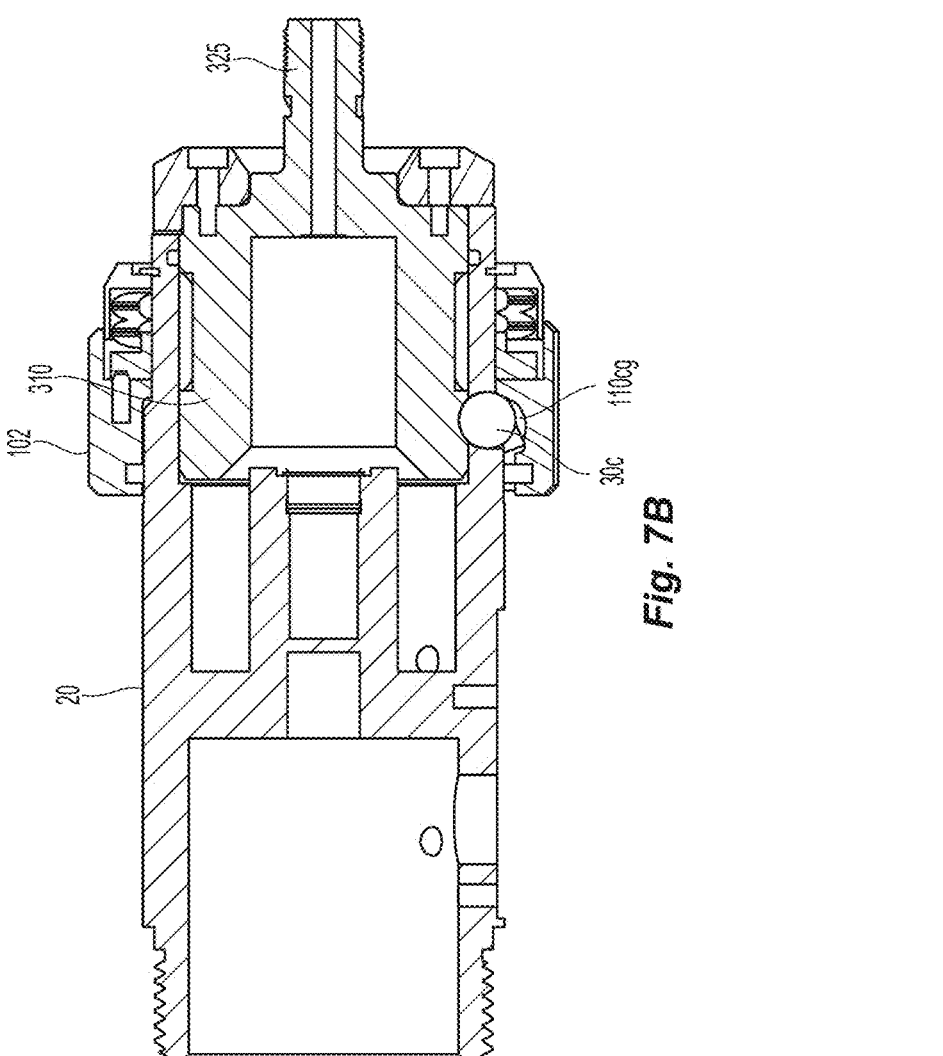

Turning now to FIGS. 7A-7C, the user rotates the collar 102 to move the tool 300 between the soft locked position and the fully locked position. Initial rotational movement in the direction "R" of the collar 102 overcomes the forces required to dislodge the collar 102 and sphere 30a-30c engagement from within first pockets 110a1-110c1. Each sphere 30a-30c guides the collar 102 along a corresponding groove 110ag-110cg as each sphere transitions towards a respective second pocket 110a2-110c2. The spheres 30a-30c remain within the recesses 350a-350c of cylinder 310 as the collar 102 rotates. Grooves 110ag-110cg are configured to vary in depth relative to the center axis "C" of the cylinder 310 (e.g., radius of the outer peripheral edge of each groove 110ag-110cg varies) such that a respective gap $G_a$, $G_b$, $G_c$ defined therebetween decreases towards the second pocket 110a2-110c2. As a result thereof, continued rotational movement of the collar 102 in the direction R enables the spheres 30a-30c to provide more inward locking force between the tool 300 and the outer housing 20.

FIGS. 8A and 8B show the tool 300 in a locked position with the collar 102 fully rotated to the $R_L$ position and the spheres 30a-30c seated within the second pockets 110a2-110c2. The tool 300 is now locked and ready for use. Turning the collar 102 in the opposite direction of R will move the collar 102 along the spheres 30a-30c from the fully locked position to the soft locked position.

Figure 9B:
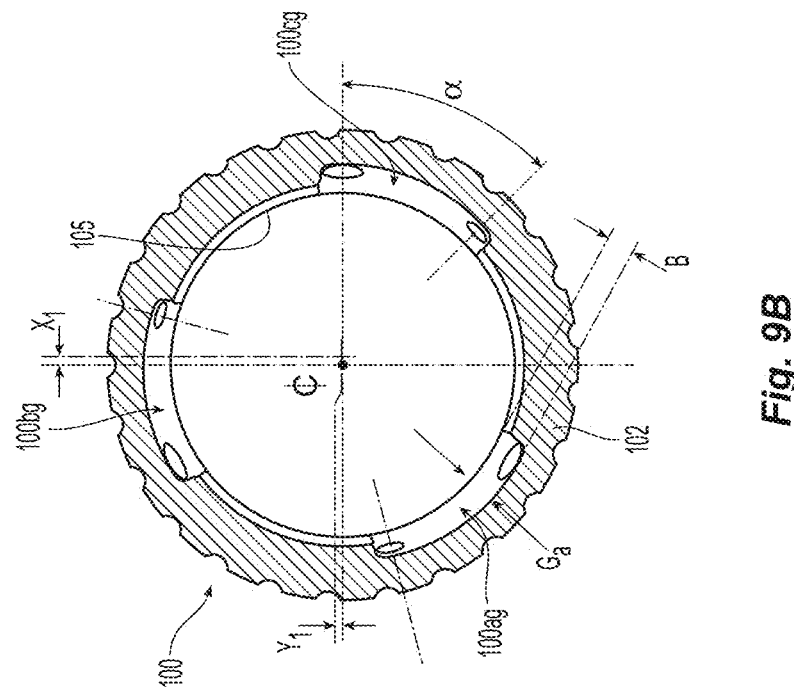
FIGS. 9A and 9B are various views of the collar of the collar locking assembly showing the details of the grooves and an example of a rotation angle for going from a soft locked position to a locked position with the collar locking assembly.
Figure 9A:
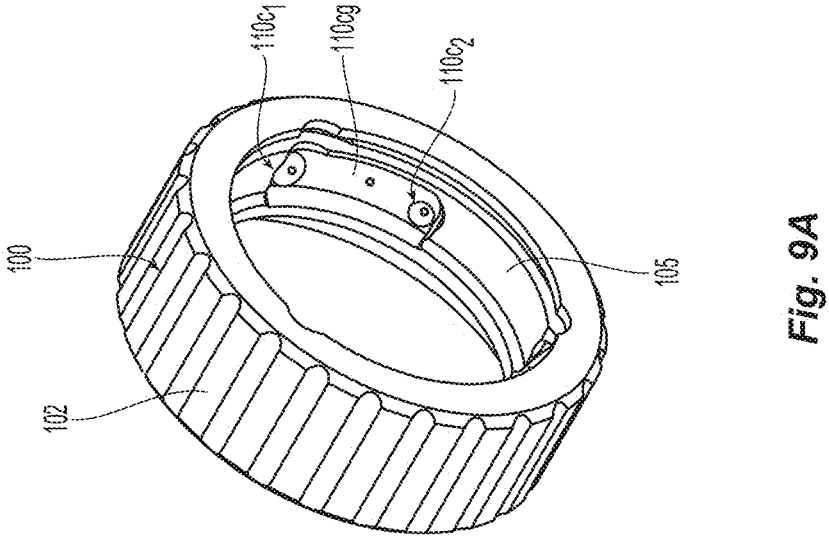

FIGS. 9A and 9B show the collar assembly 100 including the internal components associated therewith including the first and second pockets, e.g., pockets 110c1 and 110c2, groove 110cg and the inner peripheral surface 105. FIG. 9B shows the center axis "C" of the cylinder (which translates through to the collar 102) and also the envisioned radial offsets of the grooves 110ag-110cg along both the X and Y axes relative thereto, e.g., an offset distance X1 along the X axis and an offset distance Y1 along the Y axis. The collar 102 includes a rotation angle α from the soft locked position to the locked position. Angle α may vary from about 15 degrees to about 300 degrees. Alternatively, the grooves 110ag-110cg may be twisted to induce a higher spring force in the fully locked position compared to the soft locked position which would eliminate the need for an X or Y offset.

The gap G, e.g., gap $G_a$, may vary an angle β from about 30 degrees to about 100 degrees between the pockets 110c1 and 110c2. The pockets, e.g., pockets 110c1 and 110c2, may be varied in depth to facilitate locking and unlocking in both the soft locked position and the fully locked position. The fully locked pocket, e.g., pocket 110c2, may be shallower than the soft locked pocket, e.g., pocket 110c1, due to the overall locking pressure imparted by the spheres 30-30c against the cylinder head 310 associated with the change in gap G during rotation.

While several aspects of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular configurations. Those skilled in the art will envision other modifications within the scope and spirit of the claims appended hereto.

What is claimed is:

1. A surgical device, comprising:
an outer housing configured to receive a surgical tool within a cavity defined within the outer housing, the surgical tool including a cylinder configured to support a drive shaft for rotation therein; and
a collar assembly disposed atop the outer housing and configured to engage a cylinder head of the cylinder, the collar assembly including:
a collar including a step ring separating an inner peripheral surface and a spring assembly seat, the inner peripheral surface dimensioned to engage a first stepped surface atop the outer housing and the spring assembly seat configured to receive a spring assembly therein; and
at least one engagement sphere configured to operably seat within a corresponding ball pocket defined through the outer housing into the cavity, the at least one engagement sphere configured on one end to abut the cylinder head of the cylinder upon introduction of the cylinder head into the outer housing and on the opposite end to seat within a complementary at least one groove defined within the inner peripheral surface of the collar, the at least one engagement sphere configured to guide the collar along the at least one groove such that the at least one engagement sphere transitions between a first groove pocket and a second groove pocket upon rotation of the collar to secure the cylinder within the housing.

2. The surgical device according to claim 1, wherein the at least one groove varies in depth between the first groove pocket and the second groove pocket such that more force is imparted by the at least one engagement sphere on the cylinder upon rotation of the collar.

3. The surgical device according to claim 1, wherein the first groove pocket and the second groove pocket vary in depth.

4. The surgical device according to claim 1, wherein an angle of depth between the first groove pocket and the second grove pocket ranges from about 30 to about 100.

5. The surgical device according to claim 1, wherein the spring assembly includes a spring configured to provide a bias between the cylinder and the outer housing.

6. The surgical device according to claim 1, wherein the spring assembly includes a locking ring configured to retain the collar assembly atop the outer housing.

7. The surgical device according to claim 1, wherein the cylinder head includes at least one recess defined in the outer surface thereof, the at least one recess configured to complement the first groove pocket on the opposite end of the at least one engagement sphere to at least partially retain the at least one engagement sphere between the at least one recess and the first groove pocket when the cylinder head fully engages within the outer housing.

8. The surgical device according to claim 1, wherein the surgical tool includes an alignment tab extending therefrom, the alignment tab configured to operably engage a notch defined in the outer housing when the cylinder head fully engages within the outer housing, the alignment tab and notch configured to prevent rotation of the surgical tool during rotation of the collar.

9. The surgical device according to claim 1, wherein a center axis of each groove is offset relative to an axis of rotation of the collar.

10. The surgical device according to claim 1, wherein an angle of rotation of the collar within each at least one groove to transition the at least one engagement sphere between the first groove pocket and the second grove pocket ranges from about 15 degrees to about 300 degrees.

\* \* \* \* \*